United States Patent [19]

Shah et al.

[11] Patent Number: 5,505,715

[45] Date of Patent: Apr. 9, 1996

[54] IONTOPHORETIC TRANSDERMAL DELIVERY OF DEOXYSPERGUALIN COMPOUNDS

[75] Inventors: Hemanshu S. Shah; Cheng-Der Yu, both of Amherst, N.Y.; Mark A. Tepper, Issaquah, Wash.; Bhiku Patel, Amherst, N.Y.

[73] Assignee: Bristol-Myers Squibb Company, New York, N.Y.

[21] Appl. No.: 201,521

[22] Filed: Feb. 25, 1994

[51] Int. Cl.⁶ .................................................... A61N 1/30
[52] U.S. Cl. ............................................. 604/290; 604/20
[58] Field of Search ............ 604/20, 290; 607/152–153; 514/310

[56] References Cited

U.S. PATENT DOCUMENTS

| | | | |
|---|---|---|---|
| 4,710,517 | 12/1987 | Umezawa et al. | 514/616 |
| 4,996,193 | 2/1993 | Hewitt et al. | 514/11 |
| 5,207,752 | 5/1993 | Sorenson et al. | 604/20 |
| 5,215,520 | 6/1993 | Shroot et al. | 604/20 |
| 5,250,023 | 10/1993 | Lee et al. | 604/20 |

*Primary Examiner*—C. Fred Rosenbaum
*Assistant Examiner*—Mark Bockelman
*Attorney, Agent, or Firm*—Charles J. Zeller

[57] ABSTRACT

A method and system is described for the noninvasive administration of a therapeutic concentration of a deoxyspergualin compound to a patient comprising iontophoretically passing the deoxyspergualin compound through an area of the skin of the patient at a flux effective to provide the therapeutic concentration.

27 Claims, 5 Drawing Sheets

IONTOPHORETIC TRANSDERMAL DELIVERY OF DEOXYSPERGUALIN COMPOUNDS

FIELD OF THE INVENTION

The present invention concerns the iontophoretic transdermal delivery of deoxyspergualin compounds. More specifically, the present invention concerns such delivery of deoxyspergualin compounds at a flux sufficient to achieve a therapeutic dose, especially in the suppression of immune activity.

BACKGROUND OF THE INVENTION

15-Deoxyspergualin, a synthetic analog of spergualin, has the chemical structure as follows:

15-Deoxyspergualin and a process for its preparation is described in U.S. Pat. No. 4,525,299 to Umezawa et al., while U.S. Pat. No. 4,851,446 to Umezawa, deceased, et al. describes an immunosuppressing method comprising the administration of 15-deoxyspergualin and related compounds. The '299 and '446 Umezawa patents are each incorporated herein by reference thereto.

15-Deoxyspergualin has been shown to have clinical activity as an immunosuppressant, especially in the treatment of organ transplant rejection in humans. Preclinical animal models have shown activity of DSG in the treatment of rheumatoid arthritis, diabetes, lupus and multiple sclerosis. Thus, deoxyspergualin may well have efficacy in humans in the treatment of these and other autoimmune diseases such as psoriasis. Deoxyspergualin is also useful to suppress human anti-mouse antibody (HAMA) response and may have activity in treating certain types of tumors.

Beneficially, deoxyspergualin has a superior side effect profile as compared to other immunosuppressive compounds including azathioprine, prednisone, OKT3 and cyclosporin A, immunosuppressants now commonly used in the treatment of organ transplant rejections.

Disadvantageously, deoxyspergualin has a very low oral bioavailability, ranging from 2 to 6% depending on the mammalian species. The reason for this limited oral activity is likely due to its high polarity and therefore its poor penetration in the gut. Because deoxyspergualin exhibits limited passive permeation of either the gut or the skin, its administration is presently limited to parenteral infusion, for example, by intravenous, intramuscular, subcutaneous and other parenteral injection methods. Due to pharmacokinetic constraints, intravenous infusion is preferred, and typically takes about three hours. Thus, deoxyspergualin is not generally suitable for self-administration by the patient, and is limited to in-patient treatment by trained health care professionals at a hospital, clinic, etc. Moreover, such mode of administration can be unpleasant and inconvenient for the patient, and due to the need for hospital or clinic administration, increases substantially the cost of medical care. This is particularly disadvantageous in the immunosuppressive treatment of organ transplant recipients, who require chronic, often daily administration of an immunosuppressant. Such patients are thus limited in their choice of immunosuppressive agents to agents that can be administered on an out-patient basis. Therefore, these patients must often elect an agent for oral administration that has less efficacy or which causes undesirable side effects. The ability to administer deoxyspergualin by a route that would allow chronic administration would give these patients a highly desirable alternative therapy.

Applicants have now been found that deoxyspergualin compounds may be administered iontophoretically and at a flux such that a therapeutic level of deoxyspergualin is achievable in the blood stream of the patient. Accordingly, chronic and convenient out-patient administration of deoxyspergualin is possible in accordance with the present invention without using the invasive procedures of the prior art.

SUMMARY OF THE INVENTION

The deoxyspergualin iontophoretic transdermal delivery system of the present invention comprises a first electrode (variously referred to in the literature and herein as the donor or active electrode) containing an electrolytically available, pharmacologically effective deoxyspergualin compound within a suitable vehicle or carrier composition; a second electrode (variously referred to in the literature and herein as the counter, receptor or passive electrode), and a power source, the first and second electrodes each being in electrically conductive communication with said power source, the first and second electrodes further being adapted for spaced-apart physical contact with the skin or other tissue of the patient, whereby, in response to the passage of current from the power source through the electrodes, a therapeutic amount of the deoxyspergualin compound is administered to the patient.

The vehicle composition containing the deoxyspergualin compound is typically a solution, suspension or gel suitable to at least partially solubilize the deoxyspergualin compound, and may include one or more constituents adapted to enhance its penetration through the skin of the patient, or to maintain its stability in the device.

The iontophoretic delivery system of the present invention achieves a flux effective to provide a pharmaceutically effective plasma concentration of the deoxyspergualin compound in the patient's bloodstream when the system is in semicontinuous or continuous operation.

The deoxyspergualin compound delivery system of the present invention is preferably adapted for periodic replenishment of the deoxyspergualin compound contained in the donor electrode, generally not more frequently than every six hours, preferably not more frequently than every twelve hours. Most preferably, the reservoir will require replenishment not sooner than once per day. Preferably, the deoxyspergualin compound is contained in a reservoir such as a cartridge that is a removably replaceable unit of the deoxyspergualin compound delivery system, and which is disposed of when the deoxyspergualin is substantially exhausted.

DETAILED DESCRIPTION OF THE INVENTION

Deoxyspergualin

15-Deoxyspergualin ("DSG") (MW=387) and its analogs (hereinafter collectively referred to as "DSG compounds" unless otherwise specifically indicated) are molecules that have immunosuppressive activity. DSG has shown significant activity in extending allograft survival when used prophylactically in mice, rats, dogs and primates with models employing skin, kidney, heart, limb, thyroid and pancreas grafts. In addition, DSG has been shown to be effective in animal models in the treatment of autoimmune diseases like rheumatoid arthritis, diabetes and multiple sclerosis and likely will have activity in the treatment of other autoimmune diseases, for example, psoriasis.

DSG has been found to be at least as potent as other, currently marketed immunosuppressants such as cyclosporin A, azathioprine and prednisone. However, unlike these agents, DSG has been found to have immunosuppressive activity against the human anti-mouse antibody (HAMA) response in patients treated with monoclonal antibody therapy. Beneficially, DSG appears to have a superior side effect profile as compared to cyclosporin A, azathioprine and prednisone, with its dose limiting toxicity being myelosuppression. More specifically, unlike cyclosporin A, DSG is not nephrotoxic nor diabetogenic. Moreover, DSG does not inhibit interleukin-2 production, as reported with cyclosporin A. Accordingly, DSG might not suppress the patient's natural immune response to combat infection.

The major drawback with DSG is its oral bioavailability of only between about 2 to about 6% following oral administration. Accordingly, DSG is administered by invasive methods, such as parenteral injection, typically by intravenous infusion. To avoid dose-limiting toxicities, the parenteral method of administration is quite slow, generally requiring about three hours. For this reason, the use of DSG as an immunosuppressant in the treatment of autoimmune disease and in the treatment of organ transplant recipients for transplant rejection is limited to in-patient medical facilities, generally hospital facilities following surgery. DSG also appears to have antitumor efficacy, but again administration is limited to in-patient medical facilities.

Inasmuch as the treatment of autoimmune disease and organ transplant rejection requires chronic, often daily administration of an immunosuppressant, DSG administration on an outpatient basis is both impractical and expensive with the invasive administration procedures of the prior art. While oral administration of DSG would be preferred, its low bioavailability does not make it a viable dosing method. Nonetheless, it is recognized that the use of DSG on an outpatient basis either in lieu of or in combination with cyclosporin A, which can be orally administered, would be of great benefit to patients. Similarly, the noninvasive administration of DSG on an in-patient basis would alleviate the discomfort and immobility of patients presently treated by the invasive methods of the prior art.

Thus, it is easily seen that a method for the noninvasive administration of DSG and its analogs is highly desirable.

Applicants have evaluated the in vitro delivery of DSG through human cadaver skin using iontophoresis. A permeation rate of 564 µg/cm$^2$/hr across the human cadaver skin was achieved, which permeation rate corresponds to the delivery of 135 mg/day of DSG for a 10 cm$^2$ iontophoretic delivery system. This is equivalent to a dose of 2 mg/kg/day for a 70 kg average body weight person. Generally, the level of DSG delivery is linearly related to the surface area of the donor electrode. Thus, for a 20 cm$^2$ donor electrode, the delivery of 270 mg/day of DSG would be expected for a 70 kg patient, based on the flux achieved in the described experiment.

Applicants have further conducted an in vivo study to investigate the rate and extent of absorption of DSG in fuzzy rats following transdermal iontophoretic administration. Using iontophoresis, approximately 4 mg of DSG (i.e., between 15–20 mg/kg) was delivered to fuzzy rats over a three-hour period. This is equivalent to a delivery rate of about 230 µg/cm$^2$/hr of DSG. Relatively high serum levels of DSG, about 18 µg/ml, were observed after iontophoretic administration. No significant untoward dermal effects were observed due to the iontophoresis treatment.

The humoral response of animals to the foreign protein keyhole limpet hemocyanin (KLH) is used routinely as a model system to test the efficacy of immunosuppressive drugs. Activity in this model has correlated well with activity for suppressing rejection of an allograft or suppressing the development of autoimmune disease in animals. Using this model, Applicants have found that DSG delivered by transdermal iontophoresis for three days effectively suppressed the immune response in rats as compared to the control (untreated) animals. The antibody level in the treated animals on the fourteenth day following the initial treatment was still only 6% of the level of the control animals.

Deoxyspergualin and its analogs suitable for use in respect of the present invention are represented by the structural formula shown below, but without representation of the various salt species that are generally employed in the iontophoretic device:

wherein Y is an alkylene group having an even number of from 4 to 10 carbons, preferably 6 or 8 carbons, or a meta or para mono- or dialkylenephenyl radical substituent group having in total 2 to 5 carbons in the alkylene residue(s), preferably 2 to 4 carbons, and X is an alkylene or alphahydroxyalkylene radical having 1 to 5 carbons, preferably 1 to 2 carbons, or an amino acid residue, especially Gly, L-His, L- and D-ser, γ-aba and DL-HABA.

Illustrative compounds of the structure (I) are identified in Table 1 below, in which DTH is activity in delayed type hypersensitivity assays and Ab is activity at suppressing the antibody response to sheep red blood cell immunization.

Not all compounds encompassed by generic structure I appear to have therapeutic activity. Table 1 identifies certain deoxyspergualin species that have been preliminarily screened for therapeutic activity. In Table 1 those compounds for which the antibody (Ab) protocol was negative (as noted by a minus sign) are not likely to have immune suppression activity, while those compounds for which the Ab protocol was +/− may have therapeutic activity. Further studies are needed to demonstrate whether these compounds have therapeutic activity. Those compounds screening positively (+) or very positively (++) for Ab suppression are believed to have good to excellent therapeutic immunosuppressive activity. The DTH protocol provides further indication of relative therapeutic activity. DSG itself has been confirmed to have excellent immunosuppressive activity by virtue of the Examples 2 and 3, as well as clinical trials in humans. The therapeutic activity of the various DSG analogs included within generic structure I can be determined by conventional experimental methods utilizing protocols and techniques well known to practitioners of ordinary skill in the field of immunosuppression.

TABLE 1

| Y | X | DTH* | Ab* |
|---|---|---|---|
| $(CH_2)_6$ | CHOH | ++ | ++ |
| $(CH_2)_6$ | Gly | ++ | ++ |
| $(CH_2)_6$ | L-Ala | − | +/− |
| $(CH_2)_6$ | L-Leu | − | − |
| $(CH_2)_6$ | L-Phe | +/− | NT |
| $(CH_2)_6$ | L-Asp | − | − |
| $(CH_2)_6$ | L-Gln | − | NT |
| $(CH_2)_6$ | L-Pro | − | − |
| $(CH_2)_6$ | L-His | − | + |
| $(CH_2)_6$ | L-Arg | +/− | NT |
| $(CH_2)_6$ | L-Ser | ++ | ++ |
| $(CH_2)_6$ | D-Ser | +/− | + |
| $(CH_2)_6$ | L-Threo | − | NT |
| $(CH_2)_6$ | β-ala | − | NT |
| $(CH_2)_6$ | γ-aba | − | ++ |
| $(CH_2)_6$ | DL-HABA | + | + |
| $pC_6H_4(CH_2)_3$ | Gly | ++ | ++ |
| $pC_6H_4(CH_2)_3$ | L-Ser | ++ | ++ |
| $p(CH_2)_3C_6H_4$ | Gly | NT | − |
| $p(CH_2)_3C_6H_4$ | Ser | NT | − |
| $pCH_2C_6H_4(CH_2)_2$ | Ser | NT | − |
| $mCH_2C_6H_4(CH_2)_2$ | Ser | NT | − |
| $pC_6H_4(CH_2)_4$ | Ser | + | +/− |
| $pC_6H_4(CH_2)_5$ | Ser | NT | − |

*NT = Not tested

The deoxyspergualin compounds set forth above are typically used in the form of a pharmaceutically acceptable salt, for example, chloride and hydrochloride salts, especially the tri-hydrochloride salt. However, ionized deoxyspergualin compounds can also be incorporated in the iontophoretic device. Ionization is achieved by adjustment of the DSG compound vehicle solution to an acid to a slightly alkaline pH, typically between 3 to 8, preferably from about 4 to about 6.5.

Deoxyspergualin (DSG) has the structure (I) wherein Y is $(CH_2)_6$ and X is CHOH, and has shown to be incapable of passive permeation through the skin to any significant extent.

The clinically therapeutic dose of DSG is from about 0.1 to about 40 mg/day/kg of patient body weight, preferably from about 1 to about 10 mg/day/kg of patient body weight. The peak plasma concentration obtained by such dose is from about 0.1 to about 20 μg/ml. Patients achieve a $C_{max}$ of approximately 10 μg/ml of DSG at 4 mg/kg by 3 hour i.v. infusion. Because of the relatively rapid clearance of DSG from plasma, this level drops quite rapidly. Thus, six hours following intravenous injection, the plasma concentration ranges from about 20 to 200 ng/ml. A delivery system that provides for the continuous delivery of DSG and results in a steady state plasma concentration of 10 to 200 ng/ml should therefore be effective for achieving prolonged immunosuppression.

The present invention is also suitable for the delivery of the DSG compound as a racemic mixture, as well as for the delivery of the (+) and (−) isomers of DSG.

Iontophoretic Delivery of DSG Compounds

The amount of the DSG compound delivered via the iontophoretic administration method of the present invention is a function of the flux (μg/hr/cm²), the delivery surface area (cm²) and the duration of treatment (hr). To achieve the preferred steady state plasma concentration of from about 10 to about 200 ng/ml in the patient under treatment with the DSG compound, the requisite flux may be determined by the following equation:

$$J = \frac{C_{SS} \cdot Cl}{A_S}$$

where J=flux (μg/hr/cm²)

$C_{ss}$=steady-state plasma concentration (μg)

Cl=plasma clearance of the drug (ml/hr)

$A_2$=delivery surface area (cm²)

For DSG the plasma clearance is about 48,000 ml/hr. Thus, for an iontophoretic system with a 10 cm² delivery surface area, the requisite flux to achieve the aforementioned DSG steady state plasma concentration is calculated to be from about 50 to about 1000 μg/hr/cm². Accordingly, the iontophoretic delivery system of the present invention should provide a flux of at least about 50, generally from about 50 to about 1,000, preferably at least about 200 and typically between about 200 to about 400 μg/cm²/hr, based on a 10 cm² delivery system.

Surprisingly, it has been found that the high flux rates necessary to obtain the aforementioned DSG-steady-state plasma concentrations can be achieved in accordance with the present invention.

The continuous or semicontinuous administration of DSG Compounds by iontophoretic transdermal penetration is advantageous in several respects as compared to the prior art invasive procedures, as indicated above. First, the iontophoretic delivery contemplated herein permits the attainment and maintenance of a therapeutically effective steady state plasma concentration of the DSG compound. Such steady state plasma concentration, as noted above, is important to achieve from a therapeutic standpoint because of the rapid clearance of DSG compounds. The prior art invasive procedures are only able to achieve such levels by frequent invasive infusions. Secondly, the iontophoretic delivery permits a noninvasive route of administration. Lastly, iontophoresis allows the chronic delivery of DSG by the patients themselves.

Iontophoretic Delivery System

Figure 1:
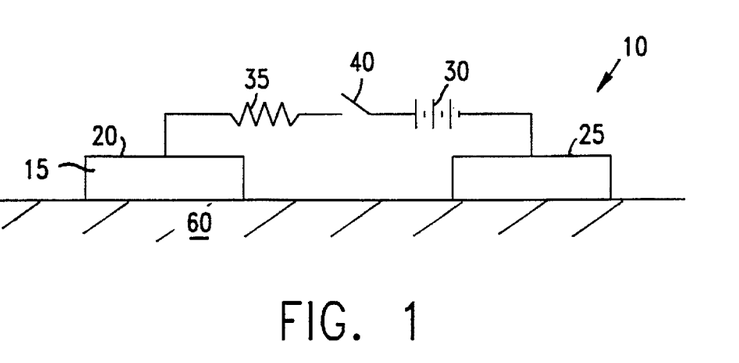
FIG. 1 is a schematic of an iontophoretic delivery device to deliver deoxyspergualin compounds in accordance with the present invention.

Referring to the schematic FIG. 1, the iontophoretic delivery system 10 to effect the transdermal administration of DSG compounds comprises a source 15 of the DSG compound to be delivered, a donor electrode 20, a counter electrode 25, and a power source 30. The donor electrode is in electrically conductive communication with the source 15 of the positively charged DSG compound and with the positive terminal of the power source 30. The counter electrode, which optionally may have a counterion source, is in electrically conductive communication with the negative terminal of the power source 30. These elements form with the skin 60 or other tissue of the patient a complete circuit to effect the migration of the DSG compound from its source 15 to the skin. Following penetration through the skin, the DSG compound is absorbed into the blood stream, whereby over time a steady state plasma concentration is achieved. The system 10 may also contain means such as variable resistor 35 to modulate the current through the system and an on/off switch 40.

Devices for the iontophoretic delivery of pharmaceuticals are known in the art. For example, the Phoresor II System manufactured by Iomed, Inc. of Salt Lake City, Utah has been used in the diagnosis and treatment of local inflammation, tendinitis, arthritis and carpal tunnel syndrome. The Phoresor II System is suitable for local use by the patient in the home after proper medical instruction and in in-patient and out-patient medical facilities. Due to size, the Phoresor II is not useful as a portable device to be worn by the patient continuously.

Portable, miniaturized iontophoretic devices are known in the art. See, e.g., U.S. Pat. Nos. 5,147,296 (Theeuwes et al.), 5,135,480 (Bannon et al.), 5,135,479 (Sibalis et al.) and 5,167,617 (Sibalis et al.), 4,585,652 (Miller et al.), each incorporated herein by reference thereto.

Figure 2:
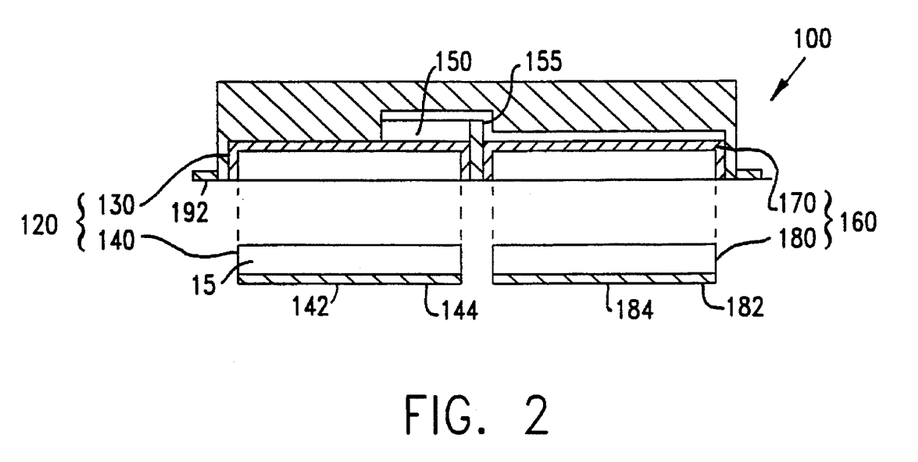
FIG. 2 is an illustrative embodiment of an iontophoretic delivery device to deliver deoxyspergualin compounds in accordance with the present invention.
Figure 3:
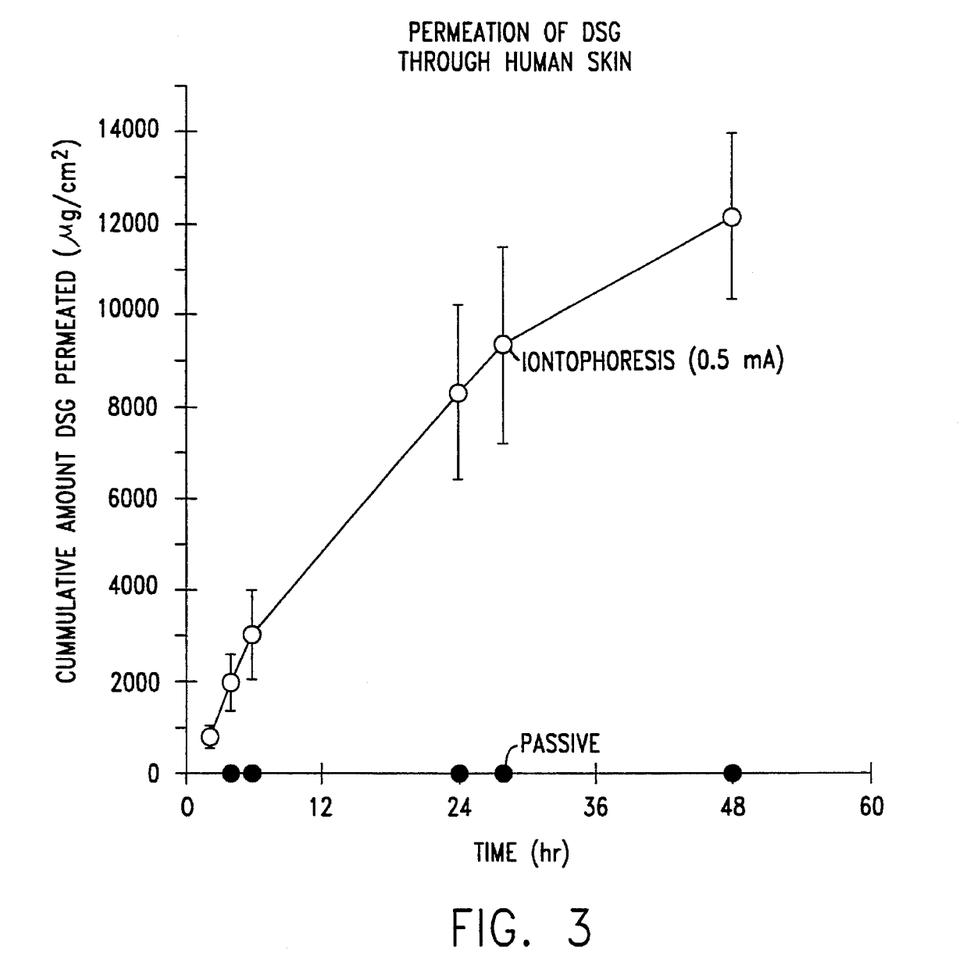
FIG. 3 is a graph of the cumulative amount of DSG iontophoretically and passively permeated through human cadaver skin versus time, based on the in vitro experiments reported in Example 1.

An illustrative embodiment of an iontophoretic device is shown in FIG. 2. The device 100 has a housing 130 of an electrically conductive material that is adapted to receive a replaceable, insertible cartridge 140, which cartridge 140 is the reservoir for the DSG compounds to be administered. The housing 130 is in conductive contact with the positive pole of a battery 150, which is the power source for the device. Together the housing 130 and the cartridge 140 comprise the donor electrode, generally shown by numeral 120. The housing 130 for the cartridge may be made of metal or of an electrically conductive polymer composite, for example, a polymer matrix in which metal powder, powdered graphite, carbon fibers and like conductive material have been incorporated.

Housing 170, similarly of an electrically conductive material, is in electrically conductive communication with the negative pole of the battery 150 through lead 155. Together with insertible counterion cartridge 180, the housing 170 forms the counterion electrode, generally shown by numeral 160. The use of the counterion cartridge is optional, but preferred as it enhances passage of current during use.

An insulative case 190 protects the electrodes 120 and 160 and the battery 150 from the environment and prevents unintended conductive contact between the several elements. The device 100 should be constructed as to permit easy, periodic replacement of the battery 150.

The cartridges 140 and 180 may comprise an external shell of an electrically conductive material within which is provided a suitable composition for containing the DSG compound or the counterion, as the case may be. The sides 142, 182 of the cartridges 140, 180 in contact with the skin of the patient may be provided with at least one permeable membrane layer 144, 184, which permits migration of the DSG compounds without leakage of the composition. A suitable membrane can be microporous, which would permit the passage of the electrolytic leak-free passage of the DSG compound. Typically, microporous membranes are made of polyethylene or polypropylene film, e.g., Celgard polypropylene film manufactured by Celanese. A peelable impervious layer (not shown) can be used advantageously to seal the cartridge prior to use.

Alternately, the DSG compound may be contained in an electrically conductive gel or impregnated in an absorbent material within the external shell of the cartridge 140. In another embodiment, the DSG compound may be contained within a conductive polymer matrix which is provided as the cartridge 140.

The electrodes may be secured on the body of the patient by any suitable means, especially by adhesive means. Thus, the reservoir may include a peripheral flange 192 with adhesive on its undersurface. Alternately, the adhesive may be on the undersurface of the membranes 144, 184 provided the adhesive does not interfere in the transport of the DSG compound from the reservoir.

While the DSG source is preferably removable from the iontophoretic delivery system to permit periodic replacement, a unitary device can be used in which a reservoir is provided with a serum stopper for DSG replenishment by means of a syringe, e.g., as described in U.S. Pat. No. 4,722,726 to Sanderson et al.

Many iontophoretic treatment devices having specialized circuitry are known in the art. Thus, U.S. Pat. No. 4,340,047 to Tapper et al. describes an iontophoretic apparatus that provides a unidirectional treatment current which is periodically interrupted by a relatively short pulse of current in the opposite direction. U.S. Pat. No. 4,406,658 to Lattin et al. describes a device with reversible polarity. U.S. Pat. No. 5,042,975 to Chien et al. describes circuitry to generate square-, sinusoidal- and triangular-trapezoidal electrical waves. U.S. Pat. No. 4,822,334 to Tapper discloses an electrical dosimetry control for use with an iontophoretic treatment device. U.S. Pat. No. 5,135,479 to Sibalis et al. discloses a programmable control and mounting system for a transdermal drug applicator. Each of these patents is incorporated herein by reference thereto. Advantageously, means to indicate power source failure, current regulation means as previously mentioned, and other safety and ease of use features can be incorporated.

The power source provides a current density of from 0.01 to 5 $mA/cm^2$. Preferred current densities are from about 0.1 to 2.0 $mA/cm^2$. Nickel/cadmium batteries are suitable.

The donor and passive electrodes each provide a skin contact area of from about 1 to 50, preferably from 5 to 20 $cm^2$.

In use, the iontophoretic device of the present invention is attached to the body of the patient such that the electrode is in physical contact with the stratum corneum, which permits the passage of the DSG compound from the electrode and into the body of the patient in response to the current provided by the power source. Generally, the device is worn continuously by the patient so that a steady-state plasma concentration of the DSG compound, once achieved, can be maintained.

The source of the DSG compound contained in the donor electrode is replenished periodically, but typically not less frequently than every six hours. Preferably, the electrode is replenished not less than about once a day. Preferably, the patient is provided with an inventory of cartridges that can be inserted into the device periodically, as determined by the treating physician. For each patient, it may be necessary to carefully monitor the DSG compound plasma concentration initially in order to establish the flux necessary to achieve the therapeutic plasma concentration. Once the flux is determined for a particular patient, periodic monitoring would be sufficient.

Flux may be adjusted by the treating physician by varying the concentration of the DSG compound in the pharmaceutical composition, by increasing or decreasing the surface area of the donor electrode in contact with the stratum corneum, or by modifying the composition of the vehicle. Preferably, flux is adjusted by adjusting the current directed to the donor electrode, for example, by a transistor-based current control circuit between the power source and the donor electrode.

Another means of regulating delivery of the DSG compound is to incorporate a microprocessor into the device that would provide current discontinuously according to a predetermined regimen, e.g., operation for several hours followed by nonoperation for up to several hours. Such discontinuous operation might further be coupled to an implanted sensor which regulates operation of the device.

The Pharmaceutical Composition

The pharmaceutical composition contained in the reservoir comprises the DSG compound and the vehicle. DSG (or its analogs) is present at an initial concentration of at least 0.1 mg/ml. Generally, the composition is less than saturated with respect to the DSG compound, although saturated solutions and suspensions may be useful. Preferably, the composition initially contains 1 to 50, most preferably 1 to 20, mg/ml of the DSG compound. As the concentration of DSG decreases in the reservoir, the flux may also decrease. A constant flux may be maintainable by current regulation coupled with a suitable microprocessor and reversible polarity system.

The vehicle for the DSG compound comprises water and hydroalcoholic systems wherein the alcohol constituent is ethanol, isopropanol or other lower molecular weight mono- and dihydric alcohols that are non-irritating to the skin. Isopropyl alcohol is preferred. The ratio of water to alcohol in the hydroalcoholic system is typically 1:10 to 10:1. Aqueous hydrogels are also suitable vehicles and form the gel matrix referred to above. The hydrogel is typically formed by incorporating up to 20% of a gelling agent in the DSG-containing composition. Suitable gelling agents are hydroxypropyl cellulose, sodium carboxy-cellulose, hydroxymethyl methacrylate and polyvinylpyrrolidone. Many other suitable gelling agents are known in the hydrogel art.

The composition may also contain a functionally effective amount of one or more adjuvants, e.g., electrolytes, pH adjustors, viscosity control agents, preservatives and the like. Generally, the adjuvants are in an amount of less than 5%, often less than 1%, which amounts are suitable to provide their intended function.

The DSG compound-containing composition may further contain a penetration enhancing agent to increase the flux of the DSG iontophoretic delivery system. Suitable penetration enhancers are propylene glycol, glyceryl monooleate, lauryl alcohol, dimethyl sulfoxide and azone. The appropriate amount necessary for optimal penetration enhancement depends upon the agent selected, and may further depend on the type of vehicle chosen. Generally, the penetration enhancers are incorporated at a concentration of from about 0.05 to 10%, preferably from 0.5 to 5% by weight of the DSG-containing composition.

Preferably, the DSG composition will not irritate the skin. Suitable agents to reduce irritation include by way of example bisabolol, methyl nicotinate and capsaicin.

The counterion composition generally is an aqueous or hydroalcohol solution containing a conventional electrolyte, for example, an inorganic salt such as sodium and potassium phosphate, or an organic material such as Tris buffer. The counter electrode may also be a dried conductive polymer gel.

The present invention is further illustrated by the following examples.

EXAMPLE 1

An in vitro skin permeation study was conducted to evaluate the iontophoretic transdermal delivery of deoxyspergualin trihydrochloride (DSG) (MW=496) through human cadaver skin mounted in side-by-side glass diffusion cells. A 1.09% w/v solution of DSG was used as the donor solution. The receptor solution was 0.5M $NaH_2PO_4$ aqueous solution. A commercially available power supply (Scepter, Keltronics Corp., Oklahoma City, Okla.) was used. Platinum electrodes were used for this study. The anode was connected to the electrode in the donor side while the cathode was connected to the electrode in the receptor (counterion) fluid. A constant DC current (0.5 mA, 0.78 mA/cm$^2$) was applied for a period of 48 hours. The receptor solution was sampled at appropriate time intervals. The samples were analyzed for DSG by reverse-phase HPLC using post-column derivatization and fluorescence detection.

FIG. 3 compares the skin permeation profile of DSG using iontophoresis versus passive permeation. From FIG. 3, it is seen that there was very little passive permeation of DSG across the skin. Conversely, iontophoresis is seen to quite substantially enhance the permeation of DSG. The permeation rate during the initial 6 hour period was 564 μg/cm$^2$/hr which is equivalent to delivery of 135 mg/day for a 10 cm$^2$ delivery system. This delivery rate would provide 2 mg/kg/day of DSG for a 70 kg average body weight person. The permeation rate decreased during the later time period due to declining drug concentration in the donor compartment. This can be avoided by using a higher initial concentration of DSG in the donor solution.

EXAMPLE 2

An aqueous solution of DSG trihydrochloride (10 mg/ml) was prepared two days prior to the experiment and stored at −5° C. until the start of the experiment. This solution was kept refrigerated during the course of the experiment. The effectiveness of iontophoretic transdermal delivery of DSG was demonstrated in an in vivo study in four fuzzy rats.

Four male fuzzy rats from Harlan Laboratories (Indianapolis, Ind.) were used in this study after a one week quarantine period. The fuzzy rat is a hypotrichotic genetic mutuant of the normal albino rat. The main difference between adult fuzzy and normal haired rats is the poorly developed hair follicles in the skin of the former. As a result, adult fuzzy rats are almost devoid of hair. The fuzzy rats have an intact immune system.

A commercially available power supply (Phoresor II, Iomed, Inc., Salt Lake City, Utah) was modified to permit constant delivery of current for up to 24 hours. A dried hydrogel electrode obtained from Iomed (Trans-Q electrode) was used as the donor electrode, and had a delivery surface area of 5.7 cm$^2$ surrounded by a peripheral adhesive overlay. The counter electrode (cathode) was a similar hydrogel patch with an area of 25 cm$^2$ (5 cm×5 cm). A mixture of cold and radiolabelled DSG was used for this study. DSG solution (1.5 ml, 15.34 mg) was added to the donor electrode to reconstitute the hydrogel just prior to the experiment. The electrodes were applied to a fuzzy rat (one on either side of the spine), which was anesthetized during the three-day duration of the experiment. A current density of 0.5 mA/cm$_2$/hr was used to deliver the DSG. The treatment period was 2.5–3.0 hours.

Blood samples were taken from the tail artery during the treatment and at the end of the treatment period. The electrodes were removed after the treatment and the skin site was wiped with alcohol swabs to remove any DSG remaining on the skin surface. The fuzzy rats were housed in metabolic cages for 3 days. Urine and feces were collected daily. Blood samples, used electrodes and skin wipes, and urine were analyzed for DSG by scintillation counting. The urine samples were also analyzed by HPLC.

Figure 4:
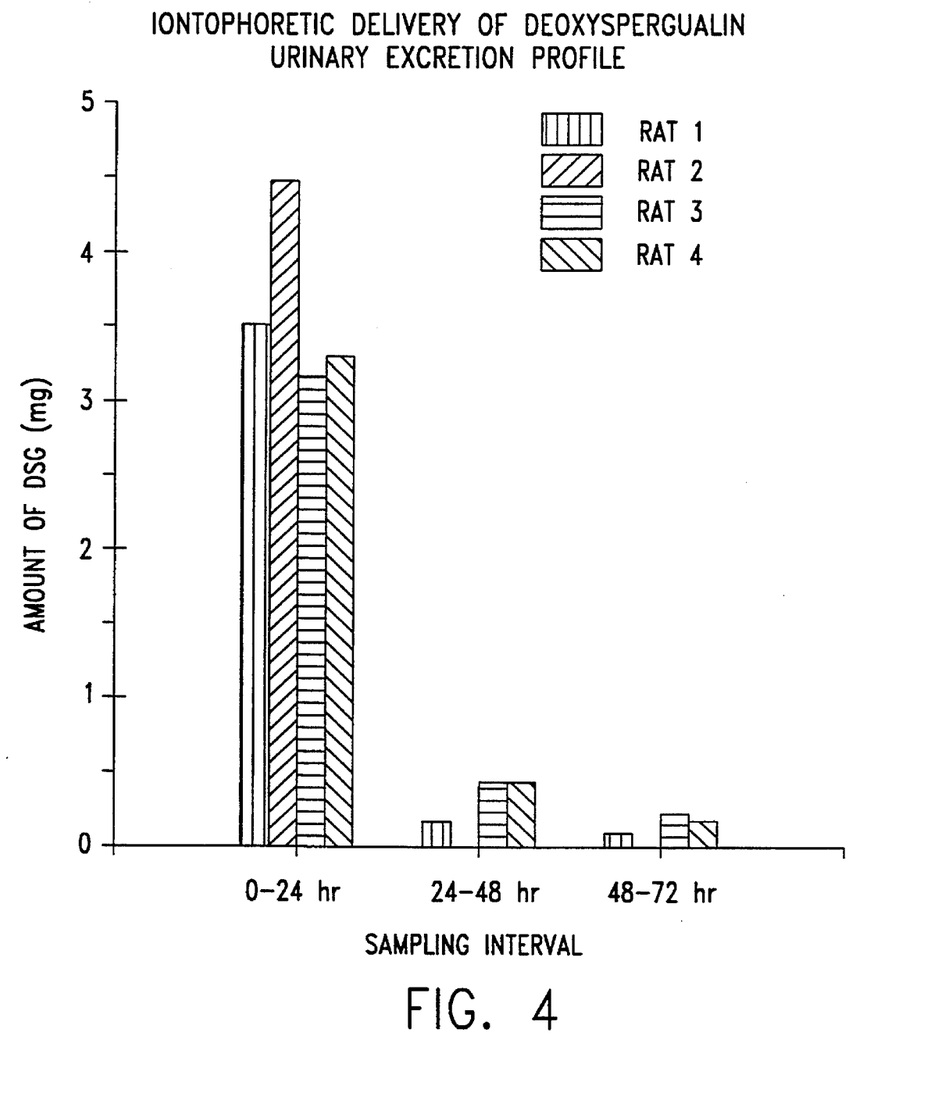
FIG. 4 is a bar graph of DSG concentration in the urine of rats receiving iontophoretically administered DSG at various time intervals, based on the in vivo experiments of Example 2.
Figure 5:
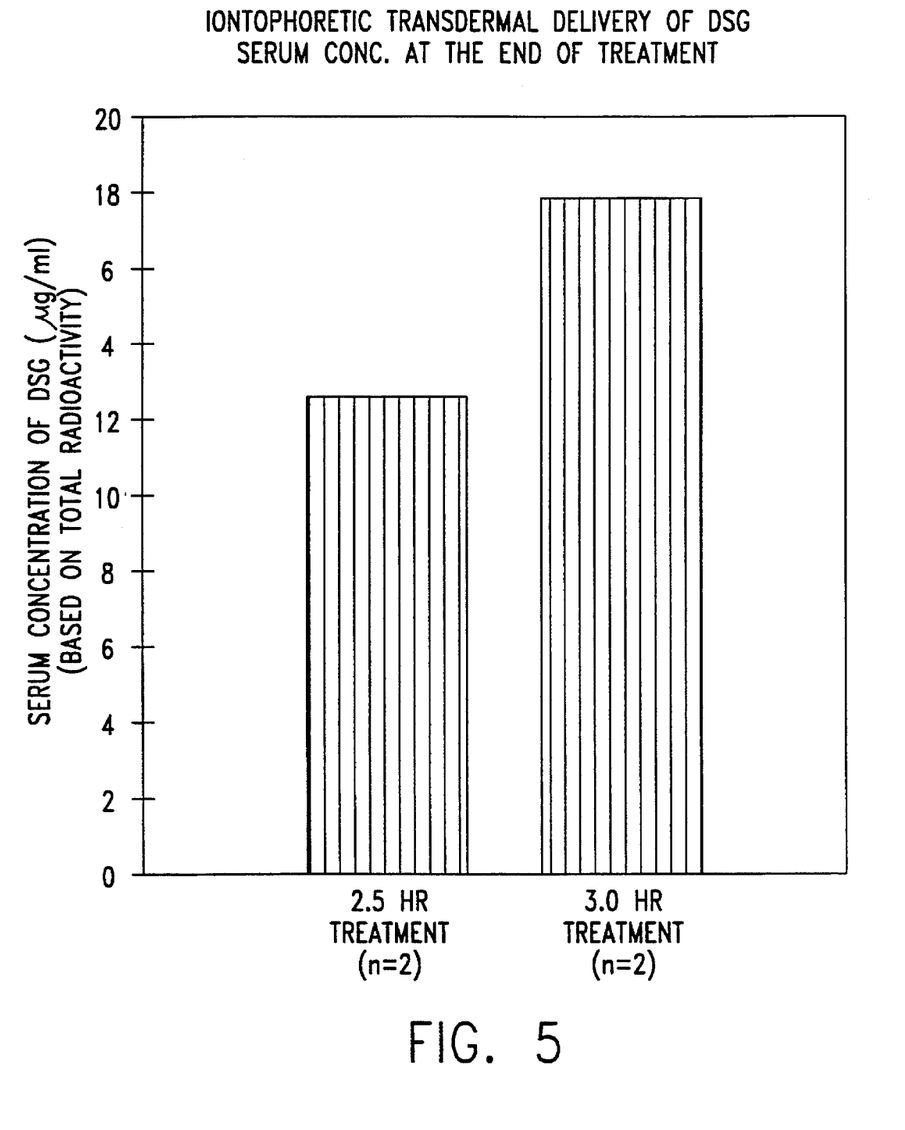
FIG. 5 is a bar graph of DSG concentration in the serum of rats receiving iontophoretically administered DSG at the end of treatment, based on the in vivo experiments of Example 2.
Figure 6:
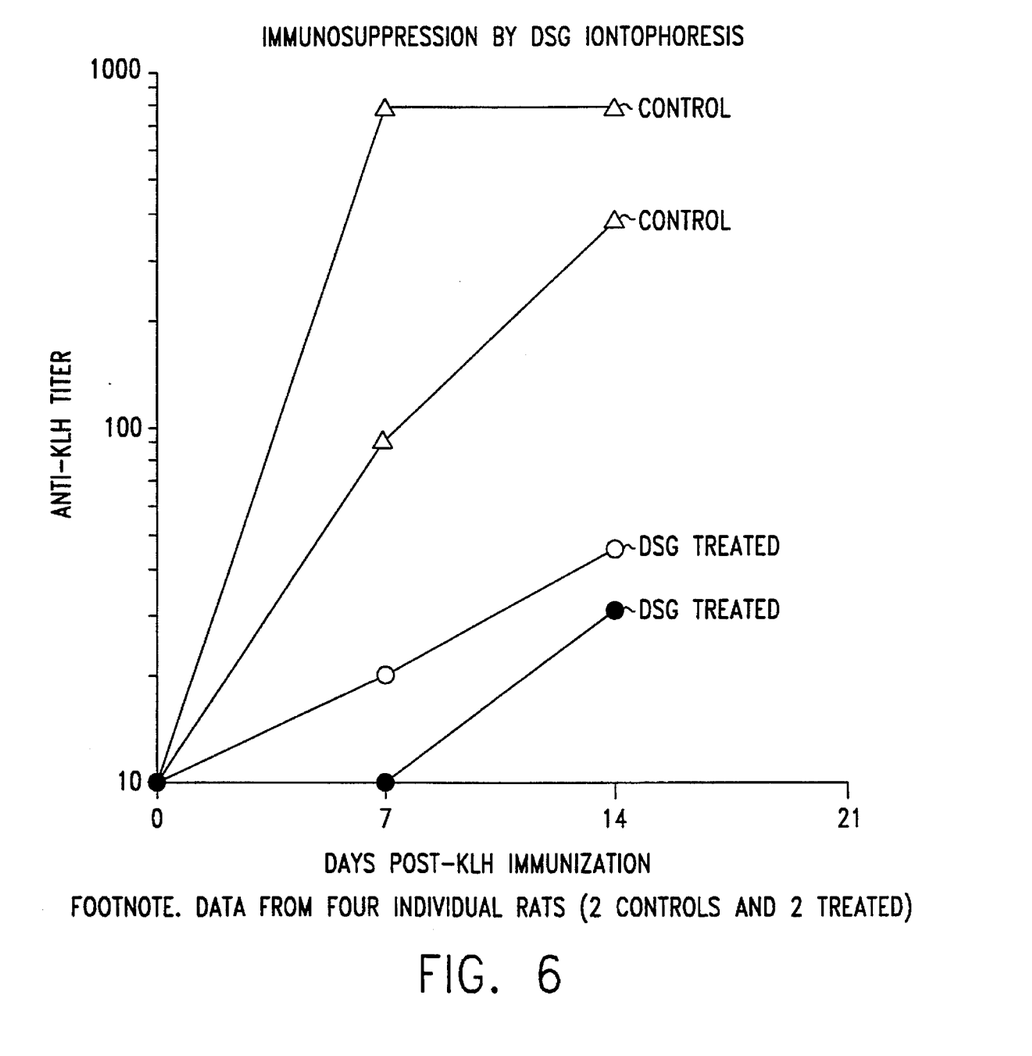
FIG. 6 is a graph of anti-KLH titer versus time for two rats receiving iontophoretically administered DSG and two untreated (control) rats, based on the in vivo experiments of Example 3.

FIG. 4 shows the urinary excretion profile of DSG for the four fuzzy rats. Based on total radioactivity recovered in the urine, an average of 3.9 mg of DSG was delivered by iontophoresis during the three hour treatment period. This is equivalent to a delivery rate of 230 μg/cm$^2$/hr of DSG. High serum levels of DSG, about 18 μg/ml, were achieved after iontophoretic delivery (FIG. 5). Based on visual observation, iontophoresis did not cause any significant untoward dermal irritation or damage.

EXAMPLE 3

The effectiveness of iontophoretic transdermal delivery of DSG trihydrochloride was further demonstrated in an in vivo immunosuppression study in fuzzy rats. Six fuzzy rats were used in this study. The procedure for this study was based on the model described by Tepper et al., *Inhibition of Antibody Production by the Immunosuppressive Agent, 15-Deoxyspergualin,* Transplant Proc., 23:328–32 (1991). This model involves immunizing the animals with a potent immunogenic antigen, keyhole limpet hemocyanin (KLH). The serum anti-KLH antibody levels (immune response) in the control and treated animals are then measured over 14 days. An effective immunosuppressive agent should result in a suppression of the immune response in the treated animals.

All six fuzzy rats were immunized with a solution of keyhole limpet hemocyanin (1 mg) by intraperitoneal injection. Two rats were used as controls and were not treated with DSG. The other four rats received DSG by transdermal iontophoresis. The electrodes and power supply used in the study of Example 2 were also used for this study. DSG solution (1.5 ml, 15.34 mg) was added to the donor (active) electrode just prior to the experiment. The electrodes were applied to each of the four participating fuzzy rats (one on either side of the spine). Prior to DSG treatment, the animals were anesthetized with METOFANE (methoxyflurane, Pitman-Moore, Mundelein, Ill.) and the hair on the dorsal side depilated. An anesthetic cocktail consisting of 10 ml of KETASET (ketamine HCL, 100 mg/ml; Aveco Co., Inc., Fort Dodge, Iowa) mixed with 2 ml ROMPUN (xylazine, 20 mg/ml; Mobay Corp., Shawnee, Kans.) was used at 0.1 ml per 100 g in order to maintain the animals under anesthesia during the treatment period. A current density of 0.5 mA/cm$^2$/hr (2.9 mA total) was used to deliver the DSG. The four rats received DSG by iontophoresis for 3 hours daily over a period of three days (Days 0, 1 and 2) (Day 0 was the first day of the experiment). During this period food and water were provided ad libitum and these four animals were housed individually in metabolic cages so that urine could be collected for analysis. On Day 3 the animals were weighed and then returned to their regular cages for the remaining duration of the study. Two rats died before Day 7, possibly due to the high levels of DSG that were being delivered. Based on the dose of DSG delivered, most animals received a dose proximate to the maximum tolerated dose (MTD) of DSG. Blood samples (0.5 ml) were collected on Days 7 and 14 from the tail artery of the remaining treated and control animals. For this purpose, the animals were anesthetized with METOFANE.

The blood samples were stored on ice for 1 hour to coagulate and then centrifuged. The serum was separated and analyzed using an ELISA method described below. Urine and cage wash samples for each collection interval were combined and the volume brought up to 40 ml. Aliquots were analyzed by HPLC.

KLH ELISA: A 96-well microtiter plate (Immulon I, Dynatech Labs, Chantilly, Va.) was coated with 50 ng/well KLH in 0.01 mol/l sodium carbonate buffer (Ph 9.6) and incubated at 4° C. overnight. The wells were then washed with 0.05% solution of PBS/TWEEN 20 in phosphate buffered saline (PBS). The nonspecific sites were blocked by incubation with 2.5% bovine serum albumin (BSA in PBS) in PBS. The wells were washed five times with the PBS/TWEEN 20 solution. The serum samples were diluted with 1% BSA in PBS and added to the wells. After incubation for 2 hours at room temperature, the wells were washed and a diluted (1:7500 in 1% BSA in PBS) solution of a rabbit anti-rat IgG peroxidase conjugated antibody (TAGO) was added. After incubation for 1 hour at room temperature, the plate was washed, developed with ABTS substrate (Kirkeguard and Perry Laboratories, Gaithersberg, Md.) and the optical density read at 405 nm. Antibody titers were performed over eight two-fold serial dilutions. These results are expressed as the dilution which gave titer values five-fold greater than background. The background was typically 0.040 $A_{405}$ units.

FIG. 6 shows the anti-KLH levels in the treated and control animals. DSG delivered by iontophoresis substantially suppressed the immune response in the treated animals as compared to the control. Even on Day 14, the antibody level in the treated animals was only 6% that of the controls. This study demonstrates the feasibility of delivering pharmacologically effective amounts of DSG by iontophoresis.

We claim:

1. A method for noninvasively administering a therapeutic concentration of a deoxyspergualin compound to a patient comprising the step of iontophoretically passing the deoxyspergualin compound through a predetermined area of skin of the patient at a flux of from about 50 to about 1000 μg/cm$^2$/hr wherein said flux is sufficient to maintain a steady state plasma concentration of about 1.0 ng/ml or greater.

2. The method of claim 1 wherein the deoxyspergualin compound is compound (I) or a compound pharmaceutically acceptable salt thereof:

(I)

wherein Y is an alkylene group having an even number of from 4 to 10 carbon atoms or a meta or para mono- or dialkylenephenyl radical substituent group having in total 1 to 5 carbon atoms in the alkylene residue(s), and X is an alkylene or alphahydroxyalkylene radical having 1 to 5 carbon atoms in the alkylene moiety, or an amino acid residue selected from the group consisting of Gly, L-His, L-Ser, D-Set. γ-aba and DL-HABA.

3. The method of claim 2 wherein Y is an alkylene group of 6 or 8 carbon atoms or a para monoalkylenephenyl radical substituent group having 2 to 4 carbon atoms in the alkylene residue, and X is an alkylene or akpnanydroxyalkylene radical having 1 to 2 carbon atoms.

4. The method of claim 2 wherein Y and X are set forth in the table below:

| Y | X |
|---|---|
| $(CH_2)_6$ | CHOH |
| $(CH_2)_6$ | Gly |

-continued

| Y | X |
|---|---|
| (CH₂)₆ | L-His |
| (CH₂)₆ | L-Ser |
| (CH₂)₆ | D-Ser |
| (CH₂)₆ | γ-aba |
| (CH₂)₆ | DL-HABA |
| pC₆H₄(CH₂)₃ | Gly |
| pC₆H₄(CH₂)₃ | L-Ser |

5. The method of claim 2, 3 or 4 wherein the steady state plasma concentration is from about 10 to about 200 ng/ml.

6. The method of claim 1 wherein the deoxyspergualin compound is 15-deoxyspergualin or a pharmaceutically acceptable salt thereof.

7. The method of claim 6 wherein the steady state plasma concentration is from 10 to 200 ng/ml.

8. The method of claim 6 or 7 wherein the flux is at least 200 μg/cm²/hr.

9. The method of claim 1, 3 or 6 wherein the deoxyspergualin compound is administered to the patient as an immunosuppressant.

10. The method of claim 1, 3 or 6 wherein the deoxyspergualin compound is administered to the patient in the treatment of psoriasis.

11. The method of claim 1, 3 or 6 wherein the deoxyspergualin compound is administered to the patient in the treatment of arthritis.

12. The method of claim 1, 3 or 6 wherein the deoxyspergualin compound is administered to the patient in the treatment of multiple sclerosis.

13. A method for the noninvasive administration of a therapeutic plasma concentration of a deoxyspergualin compound to a patient comprising the steps of affixing to the skin of a patient an iontophoretic device comprising a donor electrode having a supply of the deoxyspergualin compound, a counter electrode, and a power source, said power source being in electrically conductive communication with each of the donor and the counter electrodes, and allowing the deoxyspergualin compound to pass into and through the skin for absorption by the plasma of the patient in response to a current provided by the power source, the passage of the deoxyspergualin compound through the skin being at a flux of from about 50 to about 1000 μg/cm²/hr wherein said flux is sufficient to maintain a steady state plasma concentration of about 10 μg/ml or greater.

14. The method of claim 13 wherein the deoxyspergualin compound is compound (I) or a pharmaceutically acceptable salt thereof:

wherein Y is an alkylene group having an even number having an even number of from 4 to 10 carbon atoms or a meta or para mono- or dialkylenephenyl radical substituent group having in total 2 to 5 carbon atoms in the alkylene residue(s), and X is an alkylene or alphahydroxyalkylene radical having 1 to 5 carbon atoms in the alkylene moiety, or an amino acid residue selected from the group consisting of Gly, L-His, L-Ser, D-Ser, γ-aba and DL-HABA.

15. The method of claim 14 wherein the deoxyspergualin compound contained in the donor electrode is initially present at a concentration of at least about 0.1 mg/ml.

16. The method of claim 15 wherein the donor electrode has a skin contact area of from about 1 to 50 cm².

17. The method of claim 15 wherein Y is an alkylene group of 6 or 8 carbon atoms or a paramonoalkylenephenyl radical substituent group having 2 to 4 carbon atoms in the alkylene residue and X is an alkylene or alphahydroxyalkylene radical having 1 to 2 carbon atoms.

18. The method of claim 15 wherein the current density provided by the power source is from 0.01 to 5.0 mA/cm².

19. The method of claim 18 wherein the deoxyspergualin compound contained in the donor electrode is initially present at a concentration of from about 1 to about 50 mg/ml.

20. The method of claim 19 wherein the current density provided by the power source is from 0.01 to 2 mA/cm²/hr.

21. The method of claim 17 wherein the steady state plasma concentration is from about 10 to about 200 ng/ml.

22. The method of claim 13, 15 or 21 wherein the deoxyspergualin compound is 15-deoxyspergualin or a pharmaceutically acceptable salt thereof.

23. The method of claim 13 wherein the supply of the deoxyspergualin compound is replenished not less frequently than every six hours.

24. The method of claim 13 wherein the supply of the deoxyspergualin compound is replenished not less frequently than about once a day.

25. The method of claim 13 wherein the supply of the deoxyspergualin compound is contained in a replaceable cartridge or reservoir.

26. The method of claim 13 wherein the deoxyspergualin compound is administered continuously.

27. The method of claim 13 wherein the deoxyspergualin compound is administered discontinuously.

\* \* \* \* \*